(12) United States Patent
Vancil et al.

(10) Patent No.: US 7,821,408 B2
(45) Date of Patent: Oct. 26, 2010

(54) METHOD AND SYSTEM FOR PHYSICALLY QUALIFYING COMMERCIAL OVERLAND TRUCK DRIVERS

(76) Inventors: Dan Vancil, 51 Champions Blvd., Rogers, AR (US) 72758; Gary Moffitt, 4001 Wagon Wheen Rd., Sprindale, AR (US) 72762; Joel Whileman, 11946 Churchill Downs Dr., Sprinddale, AR (US) 92762

( * ) Notice: Subject to any disclaimer, the term of this patent is extended or adjusted under 35 U.S.C. 154(b) by 1044 days.

(21) Appl. No.: 11/276,908

(22) Filed: Mar. 17, 2006

(65) Prior Publication Data

US 2007/0219746 A1   Sep. 20, 2007

(51) Int. Cl.
*G08B 23/00* (2006.01)
(52) U.S. Cl. ...................................... 340/576; 340/575
(58) Field of Classification Search ................ 340/575, 340/576, 573.1, 436, 990; 705/2; 701/1, 701/2, 29, 36; 702/1, 182; 382/116, 118
See application file for complete search history.

(56) References Cited

U.S. PATENT DOCUMENTS

| | | | | |
|---|---|---|---|---|
| 5,717,776 A | * | 2/1998 | Watanabe | 382/116 |
| 6,313,749 B1 | * | 11/2001 | Horne et al. | 340/575 |
| 7,027,621 B1 | * | 4/2006 | Prokoski | 382/118 |
| 7,295,124 B2 | * | 11/2007 | Guillen | 340/576 |
| 2004/0064415 A1 | * | 4/2004 | Abdallah et al. | 705/50 |

* cited by examiner

*Primary Examiner*—Van T. Trieu
(74) *Attorney, Agent, or Firm*—Brent A. Capehart; Bowers Law Firm

(57) ABSTRACT

The present invention provides a system and a method for determining the physical qualification of a commercial motor vehicle driver. The system and method collect driver information from a driver, which is then assessed to determine if the driver is satisfies pre-established physical fitness qualifications. If the driver satisfies these qualifications, a certification is provided to the driver. The system and method can be executed with the aid of a computer system.

9 Claims, 6 Drawing Sheets

METHOD AND SYSTEM FOR PHYSICALLY QUALIFYING COMMERCIAL OVERLAND TRUCK DRIVERS

REFERENCE TO PENDING APPLICATIONS

This application is not based upon any pending domestic or international patent application.

REFERENCE TO MICROFICHE APPENDIX

This application is not referenced in any microfiche appendix.

BACKGROUND OF THE INVENTION

1. Field of the Invention

The present invention relates to a method and system for physically qualifying commercial overland truck drivers. More particularly, the present invention relates to a method and a system for determining whether a commercial overland truck driver is physically qualified to operate a commercial vehicle through information identification, assessment and analysis of the driver's physical condition.

2. Background

The demands on a commercial motor vehicle (CMV) driver can be very exacting. Ever changing schedule changes, long hours, tight pickup and delivery schedules, adverse road conditions all add to the physical demands of a CMV driver. Other duties, in addition to driving a large vehicle in complex driving situations, require a CMV driver to physically fit. These duties can include coupling/uncoupling trailers, loading/unloading trailers, inspecting the operating conditions of the vehicle, and lifting and installing heavy tire chains.

Before a person can legally operate a CMV within the United States, that person must be physically qualified by a United Stated Department of Transportation (USDOT) certification examiner, such as a medical examiner or a nurse practitioner, and have proof of such qualification. A person is considered physically qualified if he meets or exceeds a set of criteria established by the USDOT, which generally include having no physical impairments, no established disqualifying medical history or clinical diagnosis, no current disqualifying medical condition or clinical diagnosis, satisfactory vision and hearing ability, free of illegal substances, and has no current clinical diagnosis of alcoholism. Accordingly, a person's present medical condition, along with his medical history, must be evaluated by a USDOT certification examiner prior to being legally able to operate a commercial motor vehicle.

The typical evaluation involves an examination a driver's physical condition, both current and historical, by a USDOT certification examiner. If the driver satisfies the requirements established by the USDOT, the certification examiner will issue a qualification certificate.

This prior art examination process, however, has a number of serious deficiencies. This system lacks any type of coordination between the USDOT certification examiners and the results of the actual examinations. The current USDOT certificate is only valid for two (2) or less years. During that time, it is not uncommon for a commercial motor vehicle driver to relocate his residence, which may require the driver to be examined by a new USDOT certification examiner. The driver's physical history is typically requested from the former USDOT certification examiner, which is time consuming and delays the issuance of a new qualification certificate.

Additionally, the driver may have a physical condition, which at the time would not disqualify him from obtaining a qualification certificate but could develop into a disqualifying condition, such as increasingly high blood pressure. This type of information would be of interest to the USDOT certification examiner such that the condition could be evaluated to see if it has receded, stabilized or has worsened. The current physical examination process does not allow nor provide for this type of information.

Moreover, a driver is productive only if he is operating a commercial motor vehicle, any delay in obtaining a qualification certificate can be a hardship to the driver and/or his carrier. Considering fines and penalties can be levied against a driver and/or a driver's carrier if a driver does not have proof of his medical qualification, operating such a vehicle without a qualification certificate is not usually tolerated. Thus, any delay in the issuance of the qualification certificate, or in the event of a lost or destroyed certificate, a replacement certificate, should be minimized.

As can be seen, there is a need for a method and system for physically qualifying commercial overland truck drivers that improves upon the prior art methods.

SUMMARY OF THE INVENTION

The present invention satisfies the needs discussed above. This invention provides a simple and effective method and system for determining the physical qualification of a commercial motor vehicle driver. More particularly, this invention provides a simple and effective method to a process for enabling a USDOT certification examiner to effectively collect and analyze the physical qualification of a commercial motor vehicle driver.

One aspect of the present invention provides for a method and system for determining the physical qualification of a commercial motor vehicle driver which includes collecting driver information from a driver through a computerized client interface, assessing that information to determine if the driver satisfies pre-established physical fitness qualifications and providing certification to the driver in the event the satisfies said pre-established physical fitness qualifications.

Another aspect of the present invention provides a method and system process for determining the physical qualification of a commercial motor vehicle driver that collects driver health information including, but not limited to, driver contact information, driver health history summary information, driver vision information, driver hearing information, driver blood pressure information, driver laboratory and other test information, and driver physical examination information through a computerized client interface. This information can be stored and later retrieved within a database, accessible via a computer network.

These and other features, aspects and advantages of the present invention will become better understood with reference to the following drawings, description and claims. For a better understanding of the invention, its operating advantages and the specific objects attained by its uses, reference should be made to the accompanying drawings and descriptive matter in which there are illustrated preferred embodiments of the invention. The foregoing has outlined some of the more pertinent objects of the invention. These objects should be construed to be merely illustrative of some of the more prominent feature and applications of the present invention. Many other beneficial results can be attained by applying the disclosed invention in a different manner or by modifying the invention within the scope of the disclosure. Accordingly, other objects and a fuller understanding of the invention and the detailed description of the preferred embodiments in addition to the scope of the invention illustrated by the accompanying drawings.

BRIEF DESCRIPTION OF THE DRAWINGS

Various other objects, features and attendant advantages of the present invention will become more fully appreciated as the same becomes better understood when considered in conjunction with the accompanying drawings, in which like reference characters designate the same or similar parts throughout the several views.

DETAILED DESCRIPTION OF THE INVENTION

The following detailed description shows the best currently contemplated modes of carrying out the invention. The description is not to be taken in a limiting sense, but is made for the purpose of illustrating the general principles of the invention and the best mode for practicing the invention, since the scope of the invention is best defined by the appended claims. The invention is capable of other embodiments and of being practiced or carried out in a variety of ways. It is to be understood that the phraseology and terminology employed herein are for the purpose of description and not of limitation.

Figure 1:
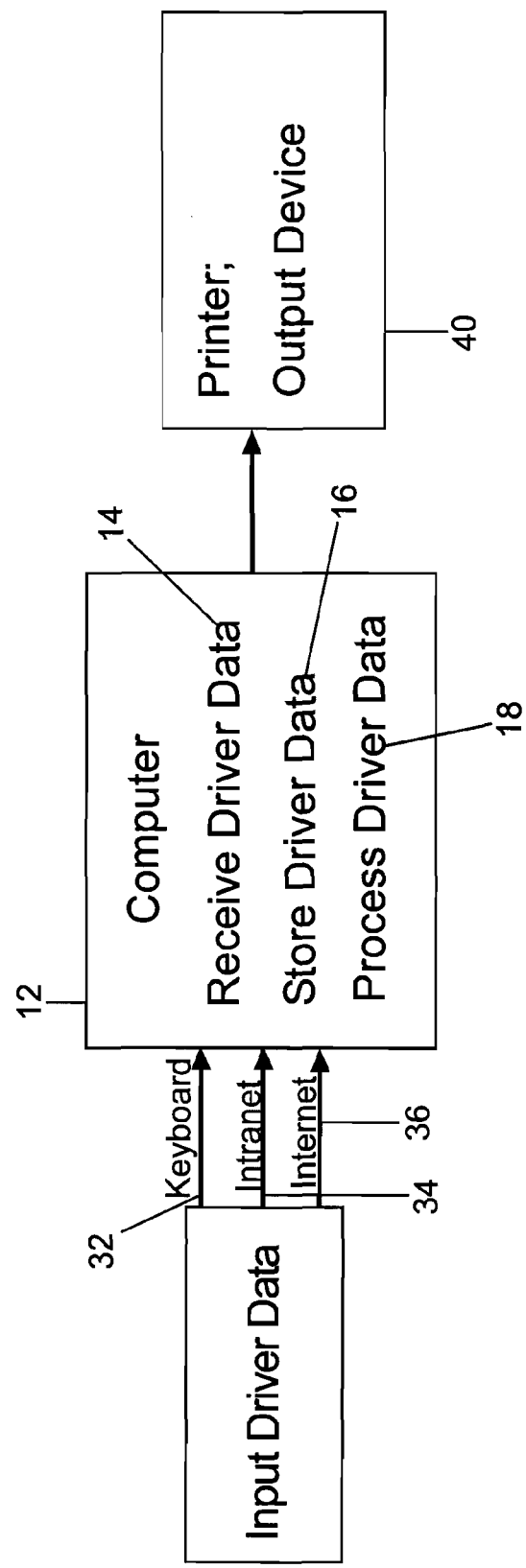
FIG. 1 is a block diagram of the system for determining the physical qualification of a commercial motor vehicle driver of the present invention.

Referring now to FIG. 1 of the drawings, there is shown a system 10, which is constructed in accordance with the present invention and which is adapted to determine the physical qualification of a commercial motor vehicle driver. The system 10 facilitates the collection and analyzing of driver health information in order to determine if that driver is physically qualified to operate a commercial motor vehicle. Such a system effectively and efficiently determines the physical qualification of a driver, provides a historical database of the physical condition of a driver, allows for job specific requirements to be considered and achieves a more thorough examination of a driver. Thus, more efficient and accurate examination results are realized.

The system 10 generally includes at least one computer 12 located within the facility of a USDOT certification examiner. Such locations would be in a medical clinic, examination room, and so forth. The computer 12 includes standard data processing, storage, display and outputting capabilities. The computer 12 allows a medical provider to input driver data 14, store the driver data 16 for later retrieval, assess the driver data to determine if the minimum physical conditions have been met 18, and if so, provide a physical condition certification to the driver 20.

The imputing of the driver data 30 can be implemented by a standard keyboard 32, remotely from a client computer 34 coupled the computer 12 via a LAN, ethernet, intranet; or from a remote off-site location via the internet or other network 36. A printer 40 is coupled to the computer 12 to enable system users to obtain hard copies of driver certifications, reports and other documents.

Figure 2:
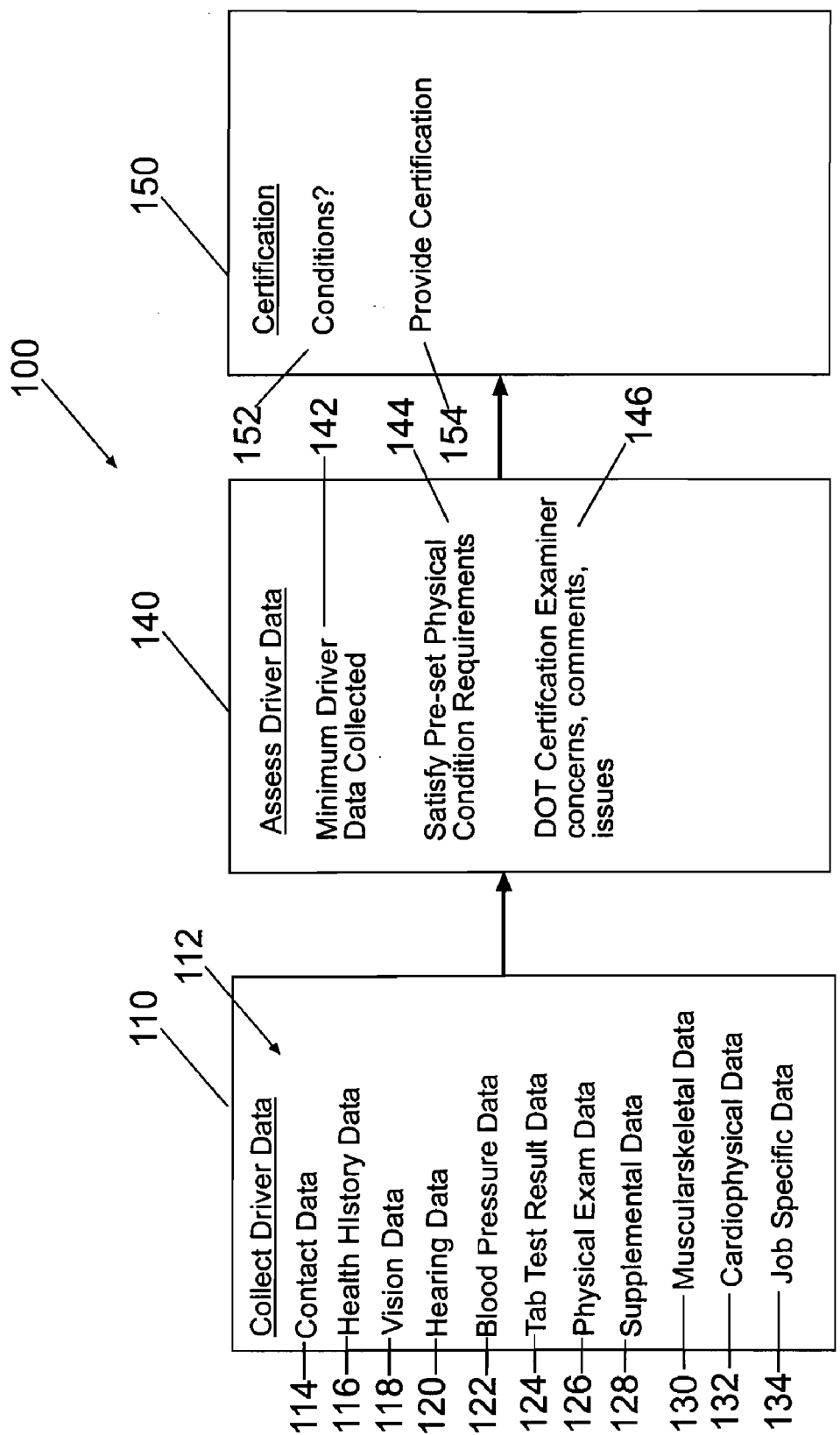
FIG. 2 is a flow diagram of a method for determining the physical qualification of a commercial motor vehicle driver the present invention.

Referring to FIG. 2 of the drawings, a block diagram of an embodiment of the process 100 to determine the physical qualification of a commercial motor vehicle driver that is in accordance with the present invention is illustrated. The process 100 includes generally a driver data acquisition component 110, a driver data assessment component 140 and a driver certification component 150.

Regarding the driver data acquisition component 110, various driver physical medical findings 112 are collected by the USDOT certification examiner from the driver through direct examination and historical review. The information is input into and stored in the computer 12. These driver health findings 112 can include, but are not limited to, general demographic information 114, vision information 116, hearing information 118, blood pressure information 120, lab test results 122, physical examination results 124, along with supplemental information 126. Supplemental information 126 can include more specific driver health information, such as musculoskeletal information 128, dynamic cardiovascular information, 130 and job specific performance information 132.

Regarding the driver data assessment component 140, the driver's health data is assessed to determine if the driver has met pre-set requirements to be physically qualified to operate an overland vehicles. In so doing, the computer 12 includes processing capabilities to determine if the minimum amount of information for each driver health aspect has been input 142 and if that information satisfies a preset qualification standard 144. Additionally, the USDOT certification examiner has the ability to input concerns and comments that augment the preset qualification standards 146.

Regarding the driver certification component 150, after a determination has been made by the certification examiner that a driver has met the pre-set requirements to be physically qualified to operate an overland vehicle, it determined if any conditions have been placed on the driver 152. These conditions can include a reduction in the amount of time the driver certificate is valid or if other requirements are imposed. These conditions are typically placed on the driver as a result of a determination by the USDOT certification examiner that the driver may have a physical condition, which at the time would not disqualify him from obtaining a qualification certificate but could develop into a disqualifying condition, such as increasingly high blood pressure. The computer 12 then produces a certificate, with or without conditions, which is available to the driver, USDOT certification examiner, overland vehicle carrier, etc 154.

Figure 3:
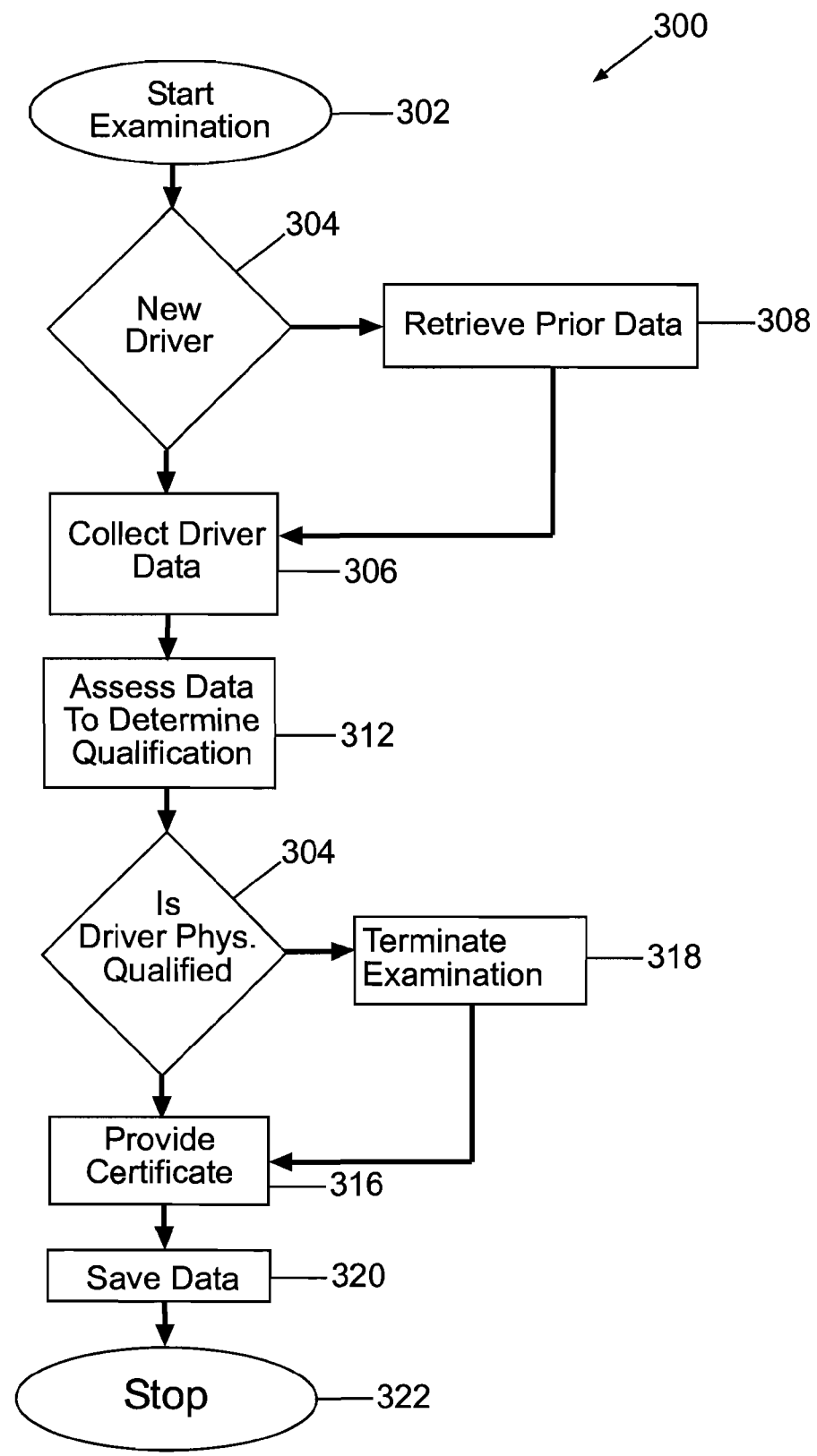
FIG. 3 is an addition flow diagram of a method for determining the physical qualification of a commercial motor vehicle driver the present invention.
Figure 4:
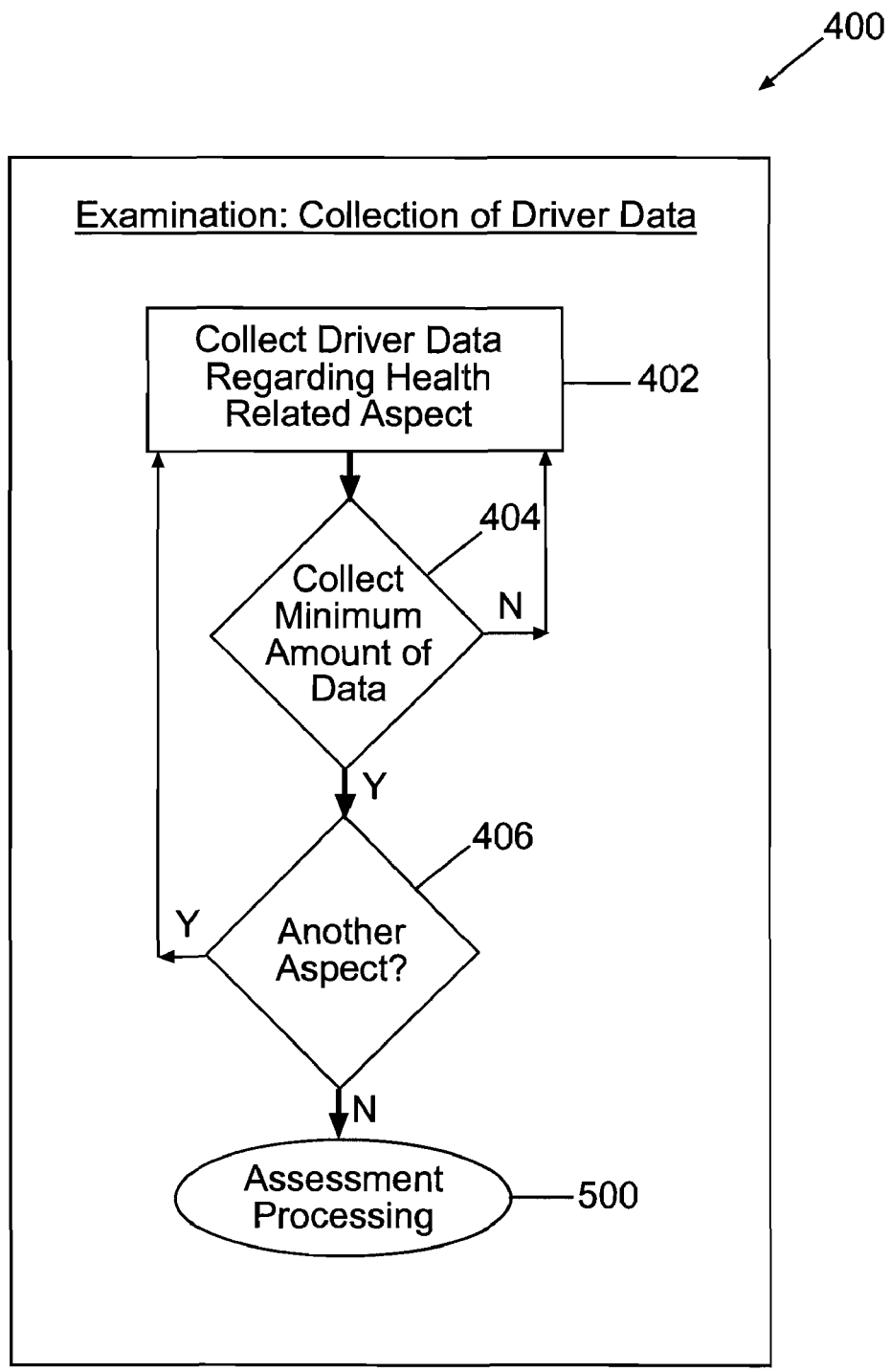
FIG. 4 is a flow diagram of an embodiment of the examination portion of the method for determining the physical qualification of a commercial motor vehicle driver the present invention.
Figure 5:
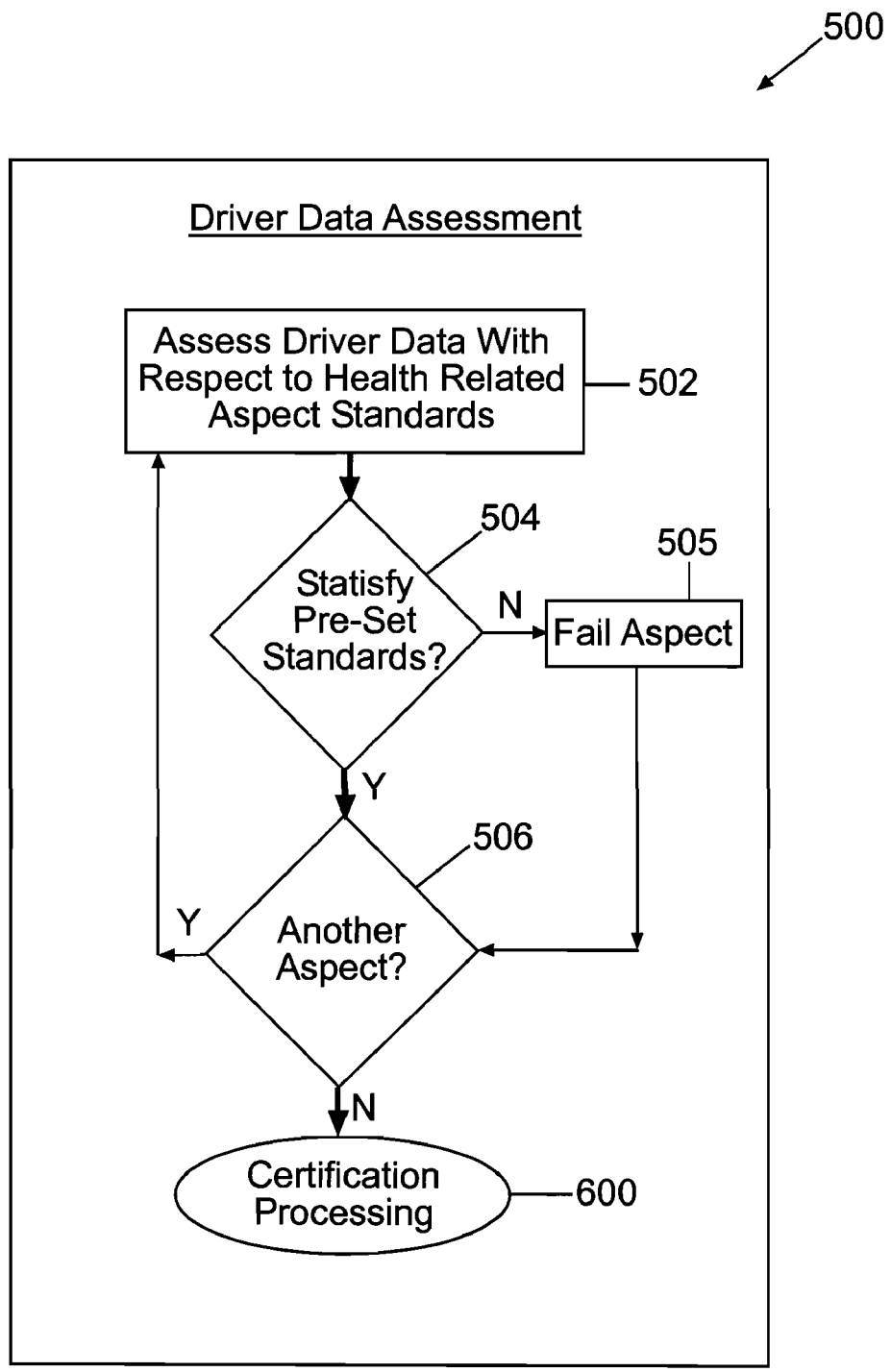
FIG. 5 is a flow diagram of an embodiment of the assessment portion of the method for determining the physical qualification of a commercial motor vehicle driver the present invention.

The method for carrying out the system 10 can best be understood by reference to the flowchart diagrams of FIGS. 3-5. Referencing to FIG. 3, a flowchart diagram illustrating an embodiment 300 of the method for determining the physical qualification of a commercial motor vehicle driver in accordance with the present invention. The embodiment 300 begins at a start instruction 302, and proceeds to an inquiry 304 that inquires if the driver examination is a new examination or a continuation of an existing examination and/or previous completed examination. If the driver examination is a new examination, embodiment 300 proceeds to driver data acquisition procedure 306. If the driver has an existing examination in process or has prior examination, that data is retrieved from a database 308. The embodiment then proceeds to the driver data acquisition procedure 306.

The procedure 306 acquires various driver data which will be utilized in determining if the driver is physically qualified to operate a commercial motor vehicle. This driver data can include a plurality of health related aspects, which can include but is not limited to, general demographic information 114, vision information 116, hearing information 118, blood pressure information 120, lab test results 122, physical examination results 124, along with supplemental information 126. Supplemental information 126 can include more specific driver health information, such as musculoskeletal information 128, dynamic cardiovascular information, 130 and job specific performance information 132.

After driver data has been acquired, the embodiment 300 proceeds to driver data assessment procedure 312. At driver data assessment procedure 312, the collected driver data is assessed to determine if it satisfies a preset level of physical conditioning 314. If the driver data satisfies the present level of physical conditioning, the embodiment 300 will pass the driver and proceed to the certification procedure 316. If, however, the driver data does not satisfy the present level of physical conditioning, the driver will be deemed to have failed the examination 318 and will not proceed to the certification procedure 316, and thus ending the examination.

Referring to FIG. 4 of the drawings, a flowchart diagram of an embodiment 400 of the driver data acquisition procedure as set out in the method for determining the physical qualification of a commercial motor vehicle driver in accordance with the present invention is illustrated. The embodiment 400 collects data regarding the health and physical capabilities of the driver from the USDOT certification examiner. The data can include a variety of health related aspects the driver's general demographic information, vision information, hearing information, blood pressure information, lab test results, physical examination results, along with supplemental information such as musculoskeletal information, dynamic cardiovascular information, and job specific information. Each of these aspects will be later assessed to determine if the driver has the minimum physical capabilities to operate an overland commercial vehicle.

Embodiment 400 starts with the collection of driver data 402 for one of the health related aspects 114-132 and then proceeds on to an inquiry 404 that inquires if a minimum amount of driver data has been input for that particular health related aspect. If the driver data does not satisfy the minimum amount of data, the embodiment 400 returns to the driver data acquisition procedure 406 for further processing. If, however, there has been sufficient information collected, the embodiment 400 proceeds an inquiry 406 that inquires as to whether driver data needs to be collected regarding another health related aspect.

If another health related aspect needs driver data, then the embodiment 400 returns to the collection of health related aspect 402. If, however, no additional health related aspect needs to driver data, embodiment 400 proceeds to a driver data assessment procedure 500.

Referring to FIG. 5 of the drawings, a flowchart diagram of an embodiment 500 of the driver data assessment procedure as set out in the method for determining the physical qualification of a commercial motor vehicle driver in accordance with the present invention is illustrated. The embodiment 500 assesses the driver data to determine if the driver satisfies preset standards for physical capabilities to operate an overland commercial vehicle.

Embodiment 500 starts with the assessing the driver data for one of the health related aspects 502 and then proceeds on to an inquiry 504 that inquires whether the driver data satisfies the preset standard for that health related aspect. If the driver data does not satisfies this preset standard, the examination is terminated 505. If, however, the driver data does satisfy the minimum standard, the embodiment 500 proceeds an inquiry 506 that inquires as to whether driver data from an additional health related aspect needs to be assessed. If the driver data of an additional health related aspect needs to be assessed, the embodiment 500 returns to the assessment of one of the health related aspects 502. If, however, no assessments need be made and all the driver data of health related aspects satisfied minimum standards, embodiment 500 proceeds to a driver certification procedure 600.

Figure 6:
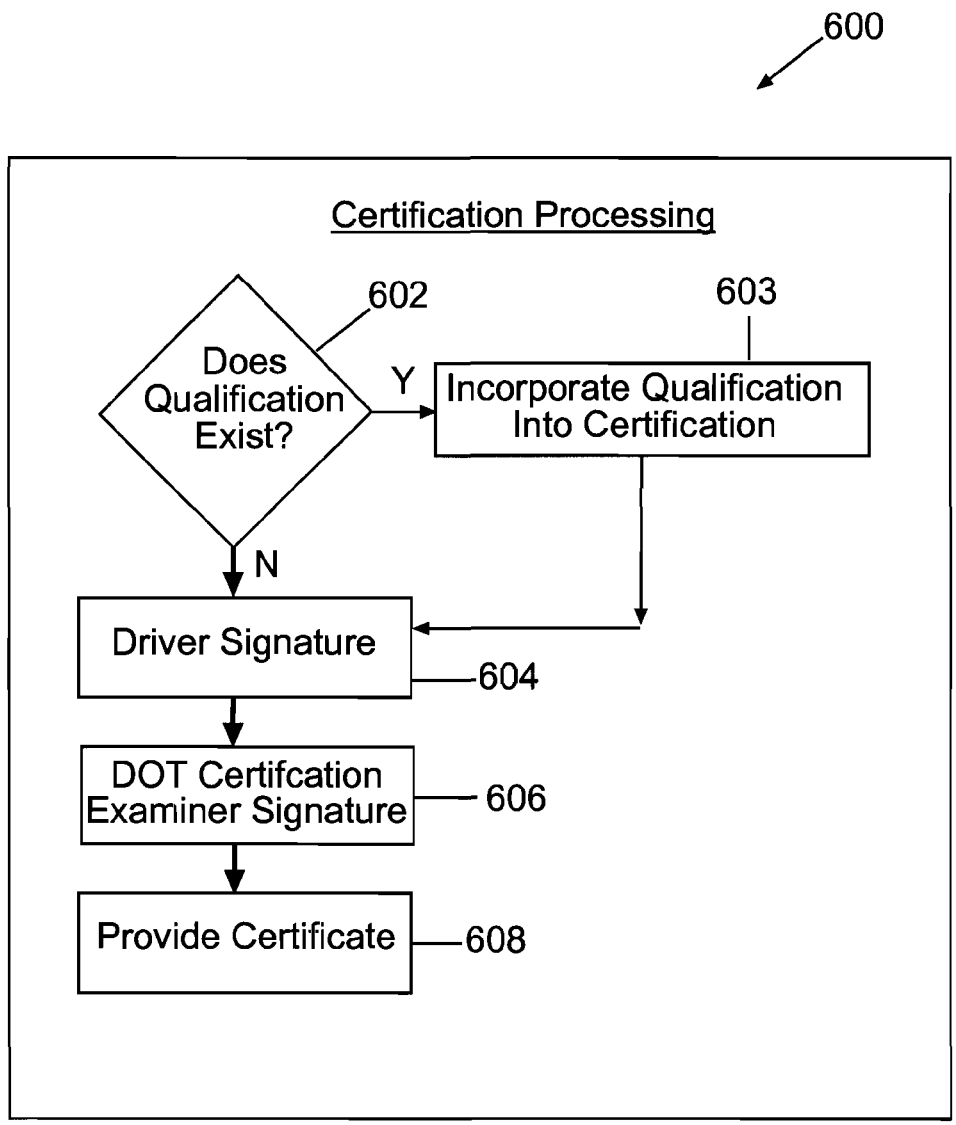
FIG. 6 is a flow diagram of an embodiment of the certification portion of the method for determining the physical qualification of a commercial motor vehicle driver the present invention.

Referring to FIG. 6 of the drawings, a flowchart diagram of an embodiment 600 of the driver certification procedure as set out in the method for determining the physical qualification of a commercial motor vehicle driver in accordance with the present invention is illustrated. The embodiment 600 processes the driver certificate after the driver has obtained a qualifying assessment of his physical capabilities to operate an overland commercial vehicle.

Embodiment 600 starts with an inquiry 602 that inquires whether any conditions have been imposed on the driver. These conditions can stem from physical conditions of the driver that may not prevent the driver from operating an overland vehicle, but could at sometime in the future cause the driver to not be physically qualified, such as increasing blood pressure or deteriorating vision or hearing. The conditions can include limitations on the actual driving abilities of the driver or a reduction in the length of time the certificate is valid. If a USDOT certification examiner determines a driver has a potential medical issue, the certification examiner could limit the validity of the driver's certificate to a time period less than the standard time of two years. Once it is determined it any conditions are present on the certification, embodiment 600 proceeds to obtain the signature of the driver 604 on the examination and the signature of the USDOT certification examiner 606. This signature can be either an actual signature or an electronically stored and implemented signature. The embodiment 600 then provides a copy of the certificate 608 that indicates the driver is physically qualified to operate a commercial motor vehicle driver.

While the preferred embodiments of the present invention have been described, additional variations and modifications in those embodiments may occur to those skilled in the art once they learn of the basic inventive concepts. Therefore, it is intended that the appended claims shall be construed to include both the preferred embodiment and all such variations and modifications as fall within the spirit and scope of the invention.

We claim:

1. A method for determining the physical qualification of a commercial motor vehicle driver, said method comprising the steps of:

collecting driver information by a United States Department of Transportation certification examiner from a commercial motor vehicle driver through direct physical examination of said commercial motor vehicle driver and a review of said commercial motor vehicle driver's prior physical examinations:

inputting and storing said driver information within a computer database, said inputting and storing being facilitated by computer software;

assessing said driver information to determine if said driver information satisfies pre-established physical fitness qualifications, said assessing being facilitated by said computer software;

providing certification to the commercial motor vehicle driver in the event said driver information satisfies said pre-established physical fitness qualifications.

2. The method of claim 1 wherein said driver information comprises:

driver contact information;
driver health history summary information;
driver vision information;
driver hearing information;
driver blood pressure information;
driver laboratory and other tests information ; and
driver physical examination information.

3. A physical qualification assessment system for determining a commercial motor vehicle driver's physical qualification for driving a commercial motor vehicle, said physical qualification assessment system comprising:

an inquiry component for facilitating collection of driver physical information obtained by a United States Department of Transportation certification examiner through direct physical examination of said commercial motor vehicle driver and a review of said commercial motor vehicle driver's prior physical examinations;

an assessment component for facilitating analysis of said collected driver physical information to determine if said collected driver physical information satisfies pre-established physical fitness qualifications;

a certification component for certifying the said commercial motor vehicle driver in the event said collected driver physical information satisfies said pre-established physical fitness qualifications;

a driver information database comprising collected driver physical information provided by drivers, said driver information database configured for storing driver physical information and for providing stored driver physical information to said inquiry component for assessment; and an electronic communications network for communicating said driver physical information to and from said inquiry component to said driver information database.

4. A computer assisted method for determining a driver's physical qualification for driving a commercial motor vehicle, said physical qualification assessment system comprising:

(a) collecting driver information by a United States Department of Transportation certification examiner from a commercial vehicle driver by direct physical examination of said commercial motor vehicle driver and a review of said commercial motor vehicle driver's prior physical examinations;

(b) assessing said driver information to determine if the driver satisfies pre-established physical fitness qualifications, said assessing said driver information being facilitated by computer software;

(c) providing certification to the driver in the event the satisfies said pre-established physical fitness qualifications said providing certification being facilitated by computer software; and (d) providing a web portal for sending and receiving information for facilitating any portion of steps (a)-(c).

5. The method of claim 4 wherein said driver information comprises:

driver contact information;
driver health history summary information;
driver vision information;
driver hearing information;
driver blood pressure information;
driver laboratory and other tests information ; and
driver physical examination information.

6. The method of claim 4 wherein said assessing said driver information is augmented by a United States Department of Transportation certification examiner.

7. The method of claim 6 wherein said United States Department of Transportation certification examiner is a medical examiner.

8. The method of claim 6 wherein said United States Department of Transportation certification examiner is a nurse practitioner.

9. The method of claim 4 wherein said providing certification to the driver is completed by the obtaining of the States Department of Transportation certification examiner's signature.

* * * * *